United States Patent
Bitensky et al.

(10) Patent No.: US 7,208,120 B2
(45) Date of Patent: Apr. 24, 2007

(54) CELLULAR DIAGNOSTIC ARRAYS, METHODS OF USING AND PROCESSING FOR PRODUCING SAME

(75) Inventors: Mark W. Bitensky, Waban, MA (US); Tatsuro Yoshida, Newton, MA (US); Michael G. Frank, East Lansing, MI (US); Christopher V Gabel, Sumerville, MA (US); Jure Derganc, Ljubljana (SI)

(73) Assignee: The Trustees of Boston University, Boston, MA (US)

( * ) Notice: Subject to any disclaimer, the term of this patent is extended or adjusted under 35 U.S.C. 154(b) by 0 days.

(21) Appl. No.: 09/965,644

(22) Filed: Sep. 27, 2001

(65) Prior Publication Data

US 2002/0142285 A1 Oct. 3, 2002

Related U.S. Application Data

(60) Provisional application No. 60/235,841, filed on Sep. 27, 2000.

(51) Int. Cl.
*G01N 15/06* (2006.01)
*G01N 33/00* (2006.01)
*G01N 33/48* (2006.01)
*C12M 1/34* (2006.01)
*C12M 3/00* (2006.01)

(52) U.S. Cl. .................... 422/68.1; 422/73; 435/287.1; 435/288.4; 435/288.5

(58) Field of Classification Search ............ 435/4, 435/6, 7.24; 422/58, 68.1, 101, 55, 81, 82.08
See application file for complete search history.

(56) References Cited

U.S. PATENT DOCUMENTS

| | | | | |
|---|---|---|---|---|
| 5,023,054 A | * | 6/1991 | Sato et al. | 422/82.09 |
| 5,427,663 A | * | 6/1995 | Austin et al. | 204/180.1 |
| 5,506,141 A | * | 4/1996 | Weinreb et al. | 435/309.1 |
| 6,027,623 A | * | 2/2000 | Ohkawa | 204/450 |

OTHER PUBLICATIONS

Sutton et al. (Microvascular Research (1997) 53: 272-281).*
Brody et al. (Biophysical J. (1995) 68(6) 2224-2232).*
Effenhauser et al. (Anal. Chem. (1997) 69: 3451-3457.*

* cited by examiner

*Primary Examiner*—Teresa E. Strzelecka
(74) *Attorney, Agent, or Firm*—Nixon Peabody LLP (57) ABSTRACT

A cellular diagnostic array has been developed that provides accurate and reproducible measurements of the physical parameters of individual cells en masse, including cell membrane surface area, cell volume, and excess membrane. Three differing patterns are employed. In the first design, a gradient array having rectangular shaped channels is used to capture cells and readily show the ratio of volume to surface area for the captured cell. The second silicone rubber array provided by the present invention employs an array of wedge shaped pipettes, each of which captures an individual cell. The position of the cell within a wedge is enough to rapidly determine the cell's actual surface area and volume. A third type of cellular diagnostic array according to the present invention employs an array of channels designed to deform a cell to study how well the cell responds to repeated deformations.

15 Claims, 6 Drawing Sheets

CELLULAR DIAGNOSTIC ARRAYS, METHODS OF USING AND PROCESSING FOR PRODUCING SAME

RELATED CASES

The present patent application claims the benefit of Provisional Patent Application Ser. No. 60/235,841 filed on Sep. 27, 2000 for "Cell Microchannel Analyzer".

STATEMENT REGARDING FEDERAL RIGHTS

This invention was made with government support under Contract No. N00014-98-1-0451 awarded by the Office of Naval Research. The government has certain rights in the invention.

FIELD OF THE INVENTION

The present invention relates generally to a device for analyzing physical characteristics of cells and, more particularly, to a device for analyzing physical characteristics of red blood cells using a microchannel array and methods for producing such a device and processes for using it.

BACKGROUND OF THE INVENTION

There are numerous types of cells that are regularly analyzed for diagnostic and/or research purposes. Human red blood cells are of particular interest. The mature erythrocyte, or red blood cell (RBC), is specialized for the collection and distribution of respiratory gases (i.e., $O_2$ and $CO_2$). The mammalian variety has evolved to the extreme to satisfy this function, having eliminated in the final stages of development in the bone marrow its nucleus and all of its organelles. Instead, the developed RBC acquires a resilient cytoskeleton and is filled with hemoglobin, which comprises one-third of the RBC's mass. Despite the loss of nearly all eukaryotic cellular equipment, it survives a 115 to 120 day circulatory odyssey. At the end of this circulatory period, the senescent RBCs are normally removed from the circulatory system by the spleen and broken down by splenic macrophages. In splenectomized individuals, the task of removing senescent RBCs shifts to the liver.

Analysis of a person's RBCs provides valuable information on the health of that person. However, conventional measurements of red cell status usually provide average values that integrate the entire population of cells into a single value, obscuring critical details. The Reticulocyte count is used to determine the life span of RBCs. Reticulocytes are RBCs that have just entered the circulatory system from the bone marrow. They have not yet discarded all of their messenger RNA, which allows them to be visualized using a nucleic acid stain. If blood cell generation and removal are in steady state equilibrium, the fraction of reticulocytes in the blood will be approximately 0.83%.

Mean corpuscular volume (MCV) measures the average volume of red blood cells, either electronically by a Coulter-type analyzer or calculated from the hematocrit and cell count. Although MCV and cell ages are generally well correlated, some ambiguity remains due to the size heterogeneity of newborn red blood cells. Moreover, this correlation is further influenced by the different rates of volume change, which occur in different phases of the red cell's circulatory lifespan. The size heterogeneity in newborn RBCs derives from the number of cell divisions that occur between a stem cell and a mature erythrocyte. It is necessary to define the population demographics as related to age. It is also important to measure size heterogeneity for other red cell age groups. A concise definition of red cell size heterogeneity will provide important data in the effort to chronicle the progression from red cell birth to senescence in terrestrial and microgravity environments, and will further define the relationship between cell volume and age.

Mean Corpuscular Hemoglobin Concentration (MCHC) measures the concentration of hemoglobin in the cytosol. Red cells continually lose minute amounts of denatured hemoglobin from the moment they enter the circulation. Since red cells have no lysosomes (and only low-capacity proteosomes), the principal hemoglobin losses occur through-extrusion in small membrane vesicles known as Heinz bodies. These vesicles are removed by reticuloendothelial macrophages, most importantly those in the spleen. Water losses compensate for the loss of membrane area. MCHC decreases only modestly throughout the circulatory life of a red cell. This changes more rapidly during the last two to three weeks of red cell circulation, when water losses become accelerated, resulting in red cell dehydration. This dehydration leads to about a 30 percent increase in MCHC, cell density, and an increased cytosolic viscosity for the oldest cells. While red cell cation channels (Gardos channels) are implicated in the accelerated water loss, the importance of these channels and their role in senescent red cell sequestration is not yet fully documented. MCHC and area and volume measurements are needed on single red cells throughout the red cell age spectrum. The whole population average for MCHC and area and volume hides important information about the oldest and the youngest red cell subpopulations.

The micropipetting aspiration procedure of Evans and Waugh yields highly detailed information including volume, surface area, and deformability on individual cells. However, because this-process is extremely labor intensive and slow, it is not practical to apply it to a statistically valid red cell sample, either in a research setting or as a clinical diagnostic tool. Until now, there has not been a satisfactory method to accurately measure the individual cell membrane area for large numbers of red cells.

When taken together, parallel advances in nanofabrication technologies, molecular and cellular biology, biochemistry, and physiology and pathophysiology have created a unique scientific opportunity.

Accordingly, it is an object of the present invention to provide an apparatus and method for rapidly obtaining detailed information including, but not limited to, volume, surface area, and deformability on individual red blood cells.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, a cellular diagnostic array has been developed that provides physical parameters of individual cells for larger number of cells for large numbers of cells, including surface area, cell volume and excess or "spare" membrane (a red cell's spare membrane is the membrane area which is in excess of that required to enclose the cytosolic volume when the cytosol is given a spherical shape). Three differing patterns are employed. In the first design, a gradient array having rectangular shaped channels is used to capture cells and readily show the ratio of volume to surface area for the captured cell. The second silicon chip provided by the present invention employs an array of wedge shaped pipettes, each of which captures an individual cell. The position of the cell within a wedge is enough to rapidly determine the cell's actual surface area and volume. A third type of cellular diagnostic array according to the present invention employs an array of channels designed to deform a cell to study how well the cell responds to repeated extreme shape changes. In addition, processes for using, as well as methods of fabricating, these cellular diagnostic arrays are herein provided.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 3a is a plan-view of a cellular diagnostic array according to the present invention, herein referred to as a "micropipette array", while FIG. 3b is a detailed, perspective-view of a microchannel for use within the micropipette array of FIG. 3a.

DETAILED DESCRIPTION OF THE INVENTION

The present invention was developed using the human red blood cell (RBC). However the present invention is not limited to human RBCs. In fact, the present invention may be used in the analysis of any type of cellular structure, whether such a structure is micro- or macroscopic in size, and living or non-living. Thus, hereinafter, erythrocytes and RBCs are defined to include any type of cellular structure.

A module incorporating a human erythrocyte microchannel analyzer (HEMA) according to the present invention may be used to analyze several different physical and kinetic characteristics of RBCs. A HEMA has been developed that quantifies the ratio of cell volume to cell surface area, which is herein referred to as the "gradient array." Another HEMA has been developed that not only quantifies the ratio of cell volume to cell surface area, but also the actual area and volume of individual cells. This HEMA is referred to herein as the "micropipette array" or MPA. Yet another HEMA has been developed that dynamically measures the deformability of an RBC, which is herein referred to as the "dynamic array."

For any array according to the present invention, the volume of an RBC is assumed to be fixed while the RBC traverses the HEMA and the surface area of the cell is an inelastic constraint that limits how narrow a channel the cell can squeeze through. The surface coating/lubrication procedures allow the assumption that the cell is trapped due to geometric constraints and not any form of sticking or tethering to the surfaces of the micro channels.

Figure 1:
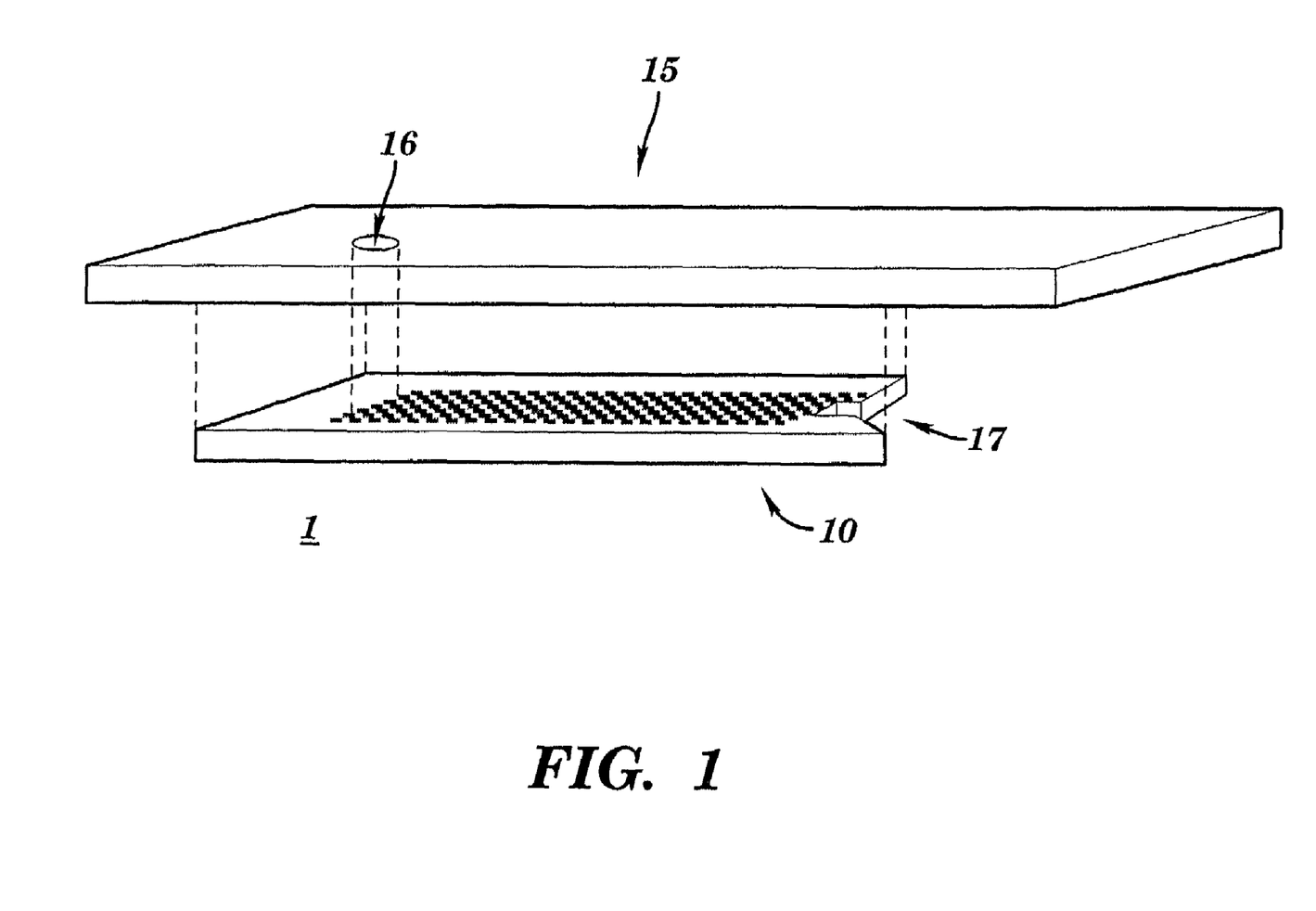
FIG. 1 is a perspective exploded view of a cellular diagnostic array module according to the present invention.

Referring to FIG. 1, there is illustrated a HEMA module according to the present invention, which is indicated as 1. HEMA module 1 comprises a HEMA 10 and a cover 15. HEMA 10 is preferably fabricated with a polymeric elastomer, such as a silicone rubber polymer. Cover 15 is preferably a standard glass microscope slide coated with elastomer within which an array entrance 16 has been made. HEMA 10 and cover 15 are preferably bonded together by plasma cleaning the surface of the polymeric elastomer, which is in fact the same polymeric elastomer with which array 10 is fabricated.

Figure 2:
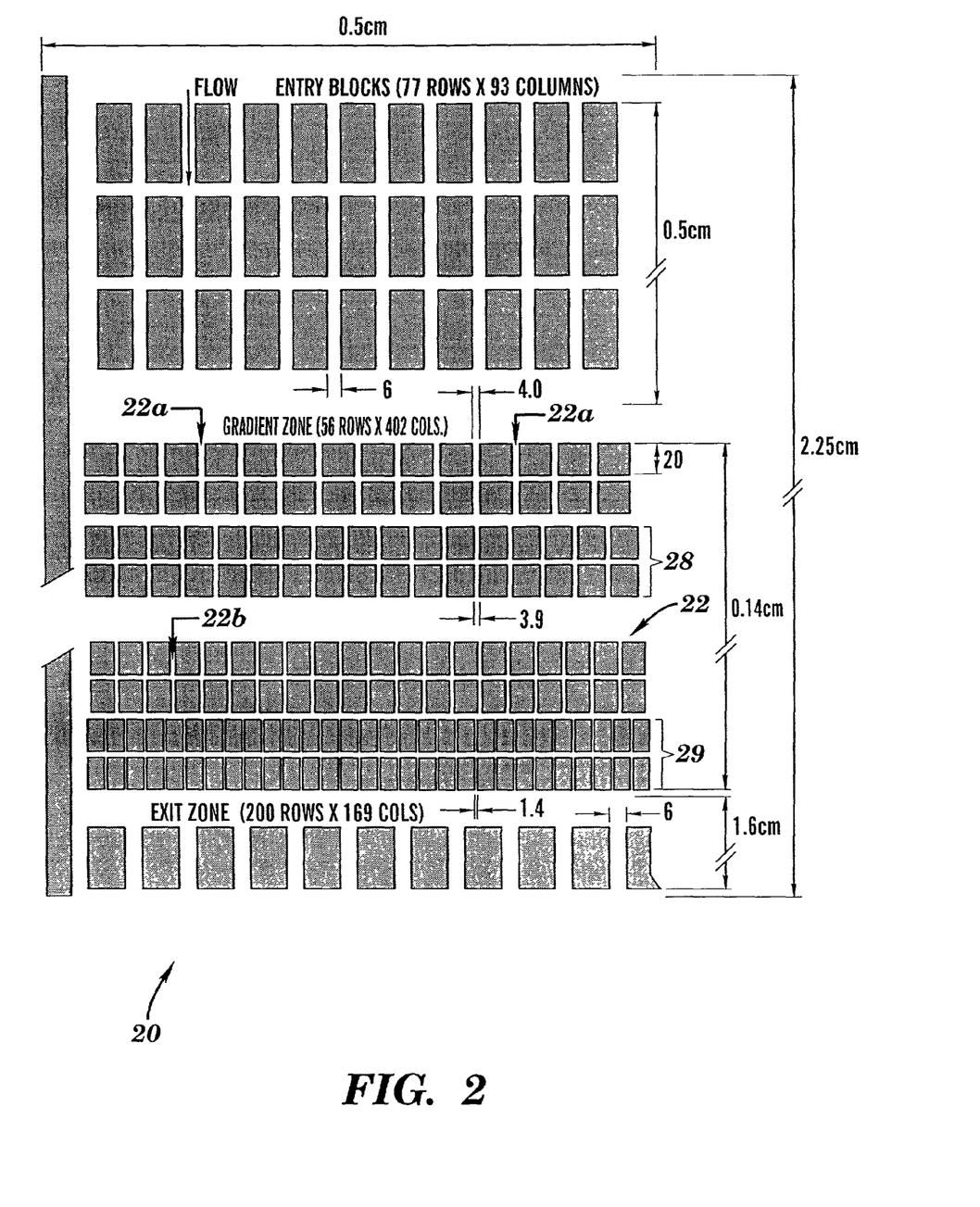
FIG. 2 is a plan-view of a cellular diagnostic array according to the present invention, herein referred to as a "gradient array".

Referring to FIG. 2, an example of a HEMA 10 is a gradient array 20. Gradient array 20 has a plurality of microchannels 22. Each microchannel 22 has a width w, a length, l, and a depth d (see FIG. 3a). While depth d preferably remains constant throughout gradient array 20, both width w and length l may be varied among the microchannels 22. Note that, for gradient array 20, each individual microchannel 22 will have constant dimensions.

Preferably, gradient array 20 also has rows of similarly shaped microchannels 22. For example, gradient array 20 may have two rows, indicated as 28 and 29. Row 28 has microchannels 22a with a first microchannel width, which is larger compared to the width of microchannels 22b in row 29. Note, however, that the number of microchannels, the number of rows, and the arrangement thereof is not limited by the examples being shown to illustrate the present invention.

The microchannel 22 that an RBC is trapped in represents the smallest microchannel 22 that such an RBC can enter, given the fact that the volume and area for a given RBC are essentially fixed quantities. The ratio of area to volume for the trapped RBC can be estimated by knowledge of the dimensions of microchannel 22 using the following equations:

$$A = 2LW + 2LH + 2\pi WTH + \pi W^2/2);$$

$$V = LHW + (\pi W^2 H/4); \text{ and}$$

$$W = 2AH - 4V - [(2AH-4V)^2 - 16H^3 \pi V]^{1/2}/(2H^2\pi),$$

where A is the surface area of the trapped RBC, L is the length of the trapped RBC, V is the volume of the trapped RBC, W is the width of microchannel 22, and H is the height_of microchannel 22.

Gradient array 20 creates a pattern of RBCs that represents the ratio of surface area to volume of a plurality of individual RBCs, as well as the initial size of those RBCs. This pattern can be used as a rough fingerprint of an individual's hematological condition in the recent past. It allows a snapshot of the past 115 to 120 days of blood production, showing not only representative individual red cell morphologies, but as well an integrated view of the entire spectrum of RBC area to volume ratios. By knowing the_width of the channel, and solving volume and area equations, a hematological profile can be generated.

Figure 3A:
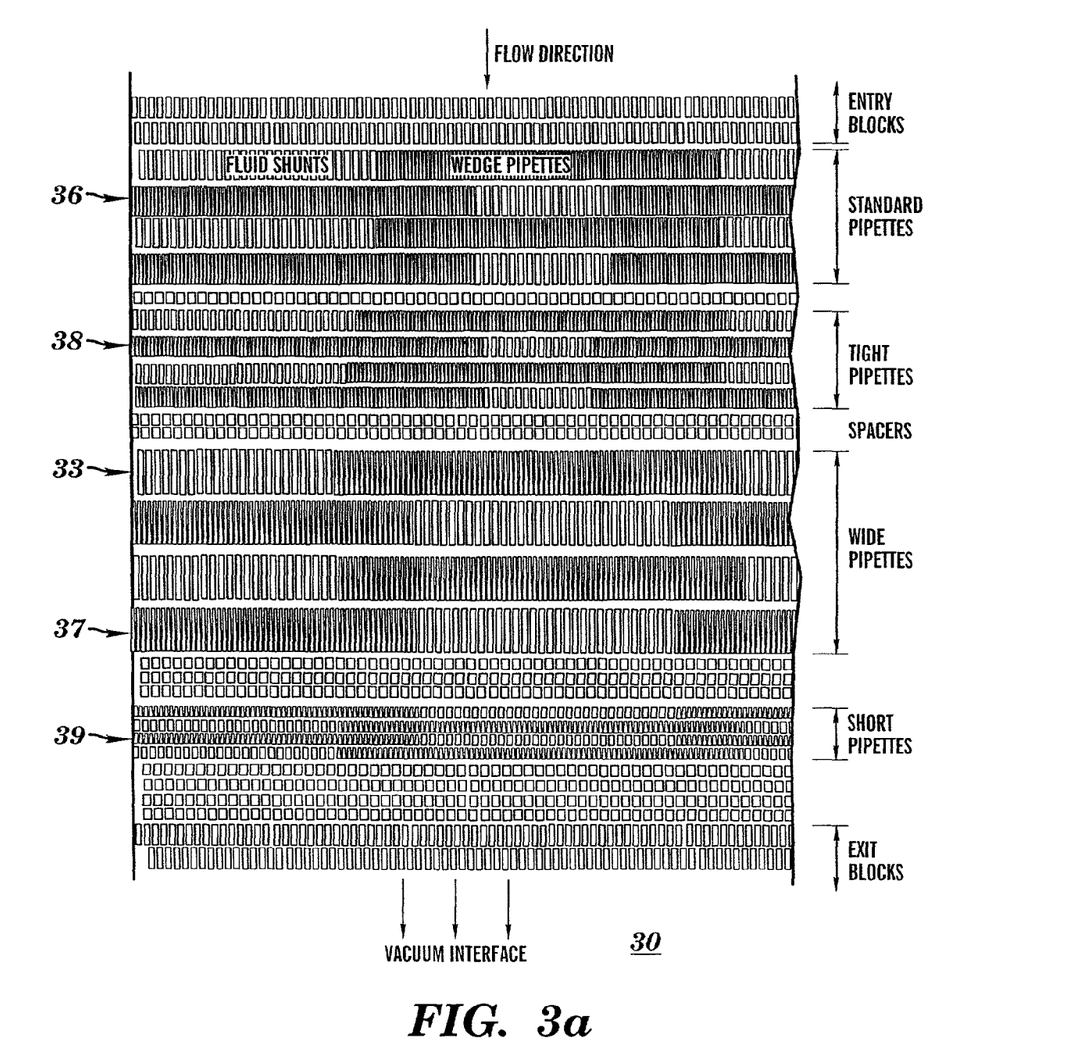
Figure 3B:
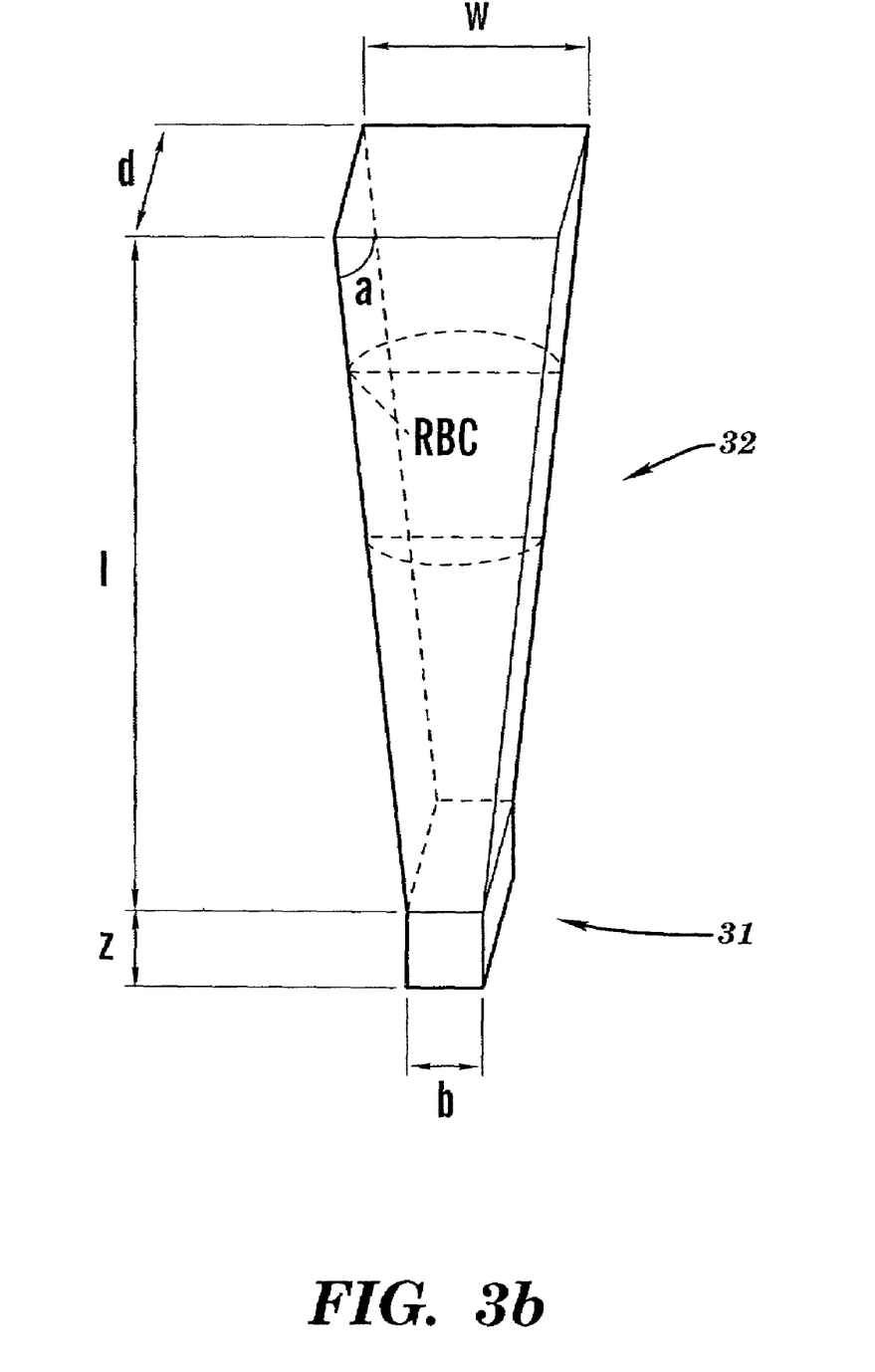

Referring to FIG. 3a, there is illustrated micropipette the array (MPA) 30, which is another example of HEMA array 10. Like gradient array 20, MPA 30 has a plurality of microchannels 32. Each microchannel 32 has a width w, a length l, and a depth d (see FIG. 3b). While depth d preferably remains constant throughout MPA 30, both width w and length l may be varied among the microchannels 32. In addition, unlike gradient array 20, each individual microchannel 32 for MPA 30 will have varying dimensions.

There are preferably at least four different geometries of wedge-shaped micropipettes in MPA 30. For instance, wide and tight pipette rows (37 and 38, respectively) are designed for cell swelling and shrinking procedures. In comparison, short pipette rows 39 are designed to prevent cells from stacking on top of each other, which makes automated data analysis difficult.

Preferred dimensions for micropipettes 32 are given in the following, table. For TABLE 1, w is the initial width of wedge-shaped micropipette 32, the length of micropipette 32, and b is the final width of micropipette 32. Chamber depth is approximately 3.4 µm. All units are in micrometers.

TABLE 1

MPA PIPETTE DIMENSIONS

| Pipette Name (Ref. # on FIG. 3) | w | B | L | # of pipettes/ row | Shunt width/length | Space between rows | # of shunts/row |
|---|---|---|---|---|---|---|---|
| Standard (36) | 3.7 | 1.5 | 60 | 300 | 25/70 | 8 | 96 |
| Tight (37) | 3.6 | 1.4 | 35 | 320 | 12/45 | 8 | 96 |
| Wide (38) | 4.5 | 1.5 | 100 | 300 | 8/110 | 8 | 100 |
| Short (39) | 3.6 | 1.4 | 16 | 300 | 14/26 | 8 | 96 |

A preferred arrangement of the four preferred types of micropipettes 32 is illustrated in FIG. 3a. As illustrated, array 30 is arranged so that, when all micropipettes 32 are full, fluid flow will continue at a constant rate through the wide "shunt channels" 33. Shunt channels 33 are designed to keep the cross sectional area of array 3.0 essentially fixed, and prevent a large pressure increase as micropipettes 32 become occupied by RBCs. Shunt channels 33 are preferably wide enough for all RBCs to pass through, and give RBCs access to all the different micropipette regions 36 ("standard"), 37 ("wide"), 38 ("tight"), and 39 ("short"), within array 30.

In order to design a micropipette 32 that would trap the maximum number of RBCs, the goal was to trap the average RBC in the middle of micropipette 32 without making micropipette 32 too long, too narrow for fluid flow, or allowing the RBC to poke out the bottom and escape. A preferred design feature is a substantially-cubical "safety channel" 31. Safety channel 31 has a cross-section smaller than that of microchannel 32 so that an RBC that makes it deep into micropipette 32 is prevented from escaping therefrom. Preferably safety channel 31 has a width equal to or less than the final width b of microchannel 32 and a length z of about 2 microns.

MPA 30 allows a more accurate method of determining not just the surface area to volume ratio of numerous RBCs, but the actual surface area and volume of individual RBCs. The surface area and volume of an RBC can be determined from the location of the top and bottom of the RBC.

When RBCs travel through MPA 30, they distribute themselves throughout microchannels 32, becoming trapped according to their individual morphology.

MPA 30 does not only differentiate cells on the basis of their sorting profile. In addition, the position of the RBC within a micropipette 32 is sufficient to rapidly determine the RBCs surface area and volume.

MPA 30 essentially mimics the action of the classic glass micropipette method, but is able to provide information on thousands of cells per trial, rather than the laborious method of one by one pipetting. The wedge shape of microchannels 22 provides an improvement in measurement resolution. As the wedge narrows, a small chance in area becomes a large change in length. By measuring the position of the top and bottom edge of any trapped RBC, the area and volume thereof can be calculated using the equations:

$$A=(T-B)/L\cdot(Y^2-X^2+(Y+X)D)+B\cdot D+D+2(B+D/\sin\theta)(Y-X)+2Z\cdot(B+D)$$

and $$V=D/2\cdot[(Y^2-X^2)(T-B)/L+2B(Y-X)]+(BDZ),$$

where T is the initial width of microchannel 32, B is the final width of microchannel 32, $\theta$ is the angle between the opening of microchannel 32 and a sidewall of the orthogonal microblocks (which run parallel to the long axis of the array), D is the depth of microchannel 32, L is the length of microchannel 32, X is the position of the top of any trapped RBC, and Y is the position of the bottom of the same trapped RBC.

Figure 4:
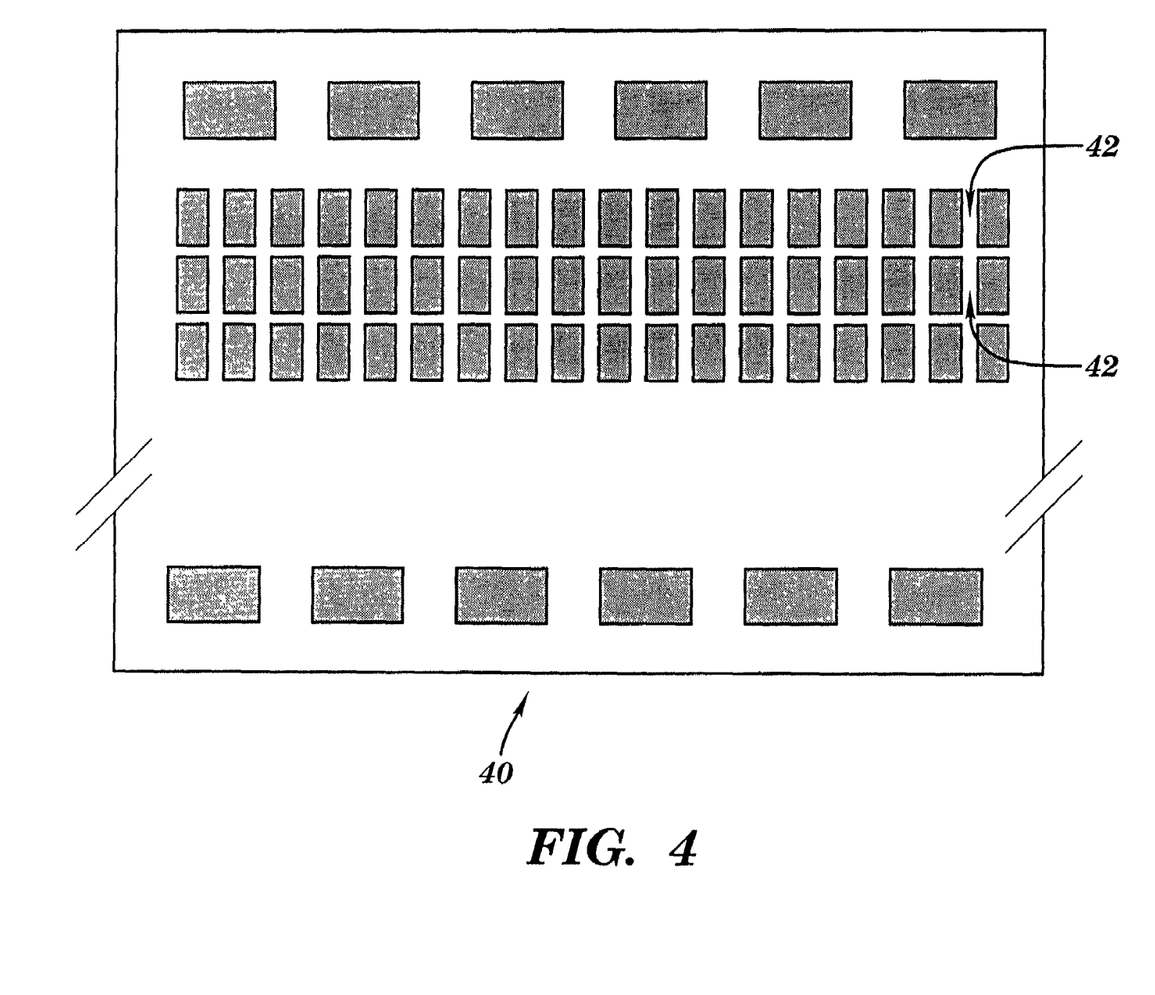
FIG. 4 is a plan-view of a cellular diagnostic array according to the present invention, herein referred to as a "dynamic array".

Referring to FIG. 4, there is illustrated a dynamic array 40, which is a third embodiment of HEMA 10 according to the present invention. Dynamic array 40 is designed to assess the deformability of individual RBCs. The deformability of the RBC greatly influences the dynamic properties of blood. For example, RBCs must be able to extend linearly and deform to enter small capillaries that can be about a third of the diameter of the fully extended, biconcave RBC. This deformation occurs over $10^5$ times throughout the life span of an RBC.

Like gradient array 20 and MPA 30, dynamic array 40 has a plurality of microchannels 42. However, unlike both previous described arrays, dynamic array 40, is not designed to trap RBCs. Rather, dynamic array 40 is designed to force RBCs to deform within microchannels 42, but ultimately to pass therethrough. Relative deformability of the RBCs within dynamic array 40 is measured by observing the transit time of the RBCs under controlled flow. As such, the dimensions of microchannel 42 will preferably be constant throughout dynamic array 40. Of course, safety blocks 31 and shunts 33, as described in reference to MPA module 30, may be used, but such design features are optional and may be used in variable configuration.

HEMA 1, 2, and 3 can be used to study a number of hematological disorders or changes involving erythropoiesis, hemolysis, and senescent or abnormal red cell sequestration. For example, patients with malignant tumors who are receiving chemotherapy are at dire risk of bone marrow suppression. A HEMA study prior to starting therapy would provide an important baseline for monitoring bone marrow function. The HEMA can also document the kinetic abnormalities in erythropoiesis and red cell sequestration in the spleen in such diseases as diabetes mellitus, thalassemia, sickle cell anemia, and liver cirrhosis with splenomegaly. It may become a commonplace practice to obtain a HEMA-generated profile (a HEMAgram) as a routine aspect of the periodic medical check-up. Specific blood analysis procedures include whole blood analysis, RBC fractionation, age cohort analysis, osmotic swelling analysis, and flow cytometry sort analysis.

For whole blood analysis using HEMA module 1, blood is extracted and diluted with an appropriate buffer solution, after which the RBCs are separated from the blood using any suitable method, such as centrifugation, and suspended in solution. The blood solution is pipetted onto array 1, 2, and/or 3 and pulled therethrough using vacuum pressure. Alternatively, the blood solution may be pushed through array 1, 2, and/or 3 using, for example, the appropriate buffer solution under pressure. The filled array is then ready to be analyzed. Preferably, the filled array is mounted on a mechanical microscope stage translation.

The following EXAMPLES describe the whole blood analysis procedure according to the present invention.

EXAMPLE 1

Whole Blood Analysis

Three mL of venous, blood was extracted with a heparinized syringe from a human volunteer. The blood was diluted to 15 mL with a HEPES 1% BSA buffer. The solution was centrifuged 4 min. at 4,000 rpm at 7° C. The buffy coat (leukocytes) was aspirated, and the cells were resuspended and centrifuged again under the same conditions. The supernatent was removed and the cells were diluted to 15 mL and kept on ice.

The array was placed on the stage and a 1% PEG (silanated polyethylene glycol) and BSA array solution was allowed to flow for 10 minutes at a pressure of 19 in. of Hg. 5 µL of the blood solution was added to 1 mL of room temperature array buffer solution. The solution was gently agitated for 5 min. at room temperature. The array pressure was reduced to 8 in. of Hg and 10 µL of the dilute blood solution was pipetted onto the array entrance interface. Pressure was reduced to approximately 0.4 in. of Hg when the first row achieved half occupancy, usually less than two minutes. The remaining cells at the entrance interface were rinsed with the buffer solution. Each row was scanned by mechanical microscope stage translation and recorded for later counting. The array was discarded after each trial.

For fractionation age cohort analysis using HEMA module 1, RBCs are separated into fractions based on size and volume/density. The various cohorts were tested with HEMA module 10 in the same manor as described in reference to whole blood analysis. An example of fractionation age cohort analysis is described below.

EXAMPLE 2

Fractionation Age Cohort Analysis

Blood cells were taken from a volunteer and separated into fractions based on size and volume. A two part procedure was used using a Larcoll density separation and a Beckman counterflow centrifugation elutriator. First the cells were sorted according to density on the Larcoll density gradient. The bottom, most dense layer was extracted, as well as the top, most buoyant layer. These two samples were then further refined by fractionation on the elutriator. The cells could be separated into different samples based on the elutriator fluid flow rate. The higher the flow rate, the larger the size of the cells extracted. Thus, each fraction of the density gradient could be subjected to a size based separation. The resulting fractions can isolate the densest. smallest cells and, on the other extreme, the lightest, largest cells.

An HPLC analysis was used to verify the increase in percent glycated hemoglobin with increasing density and decreasing size. An ion exchange column with a particle size of 2.5 µm was used. The lightest and largest cells were shown to be young cells by $H_bA1c$ content. The densest and smallest cells were shown to be the oldest by the same criterion. The various cohorts were tested on the array in the same manor as above.

Cells separated into old and young cohorts by size and density were sorted on the gradient array. The gradient array sorts cells based on their ratio of surface area to volume. Both old and young cells became trapped in essentially the same region for a given subject. This indicates that in any individual the cells are maintaining a constant surface area to volume ratio throughout their lifespan.

For osmotic swelling analysis using HEMA module 1, RBCs were again separated into age based fractions as above. Several solutions, each at a different osmolarity, are prepared and placed within array 1, 2, and/or 3. The MCV may be determined using a combination of RBC counting and percent volume calculation. An example of osmotic swelling analysis is described below.

EXAMPLE 3

Osmotic Swelling Analysis

RBCs were separated into age based fractions as above. 3 HEPES array solutions were prepared, with osmolarities of 220 mmol/kg, 310 mmol/kg, and 400 mmol/kg. The osmolarities were determined using the Vapro vapor pressure osmometer. 20 µL of diluted blood was pipetted into 1 mL of each osmotic solution. The experiment was performed as above, maintaining a five-minute acclimation time for each sample. The MCV was determined using a combination of cell counting and hematocrit measurements. A Coulter counter was used to count the number of RBCs, and a micro-hematocrit was used to determine the percent volume of cells.

When RBCs are exposed to hypotonic solution, they rapidly absorb water and swell in size. The converse is true in a hypertonic solution, where cells shrink due to loss of cytosol. The swelling is limited by the inelastic red cell membrane, wherein the lipid is strengthened by a fibrous cytoskeleton. The resulting swollen cell has an excess surface area approaching zero. This phenomena was used to separate old cells from young cells on the gradient array. Old cells have less surface membrane, and are unable to swell to as large a volume as young cells, which have considerable excess membrane. Three age_cohorts: young, normal, and old, were exposed to both hypertonic and hypotonic solutions. The young cells consistently became trapped at the widest channels. The results were not as consistent for older shrunken cells, possibly due to changes in membrane crosslinking and dehydration as red cells approach senescence.

This result has valuable clinical and scientific implications. The swelling array technique can be used to determine the relative presence or absence of young and old cells in a patient's blood. The current method, reticulocyte count, can only determine the number of cells that have been generated within the last 24 to 48 h. The array allows much greater flexibility. For example, in situations where there is no reticulocyte information, the array can be used to measure the recent history of erythropoiesis and cell sequestration in the spleen.

For flow cytometry sort analysis using HEMA module 1, a flow cytometer is used to extract reticulocytes and PS-exposing RBCs from whole blood. The reticulocytes are stained, the PS-exposing RBCs are labeled, and both types of cells are suspended in solution. The samples are then placed on array 1, 2, and/or 3 as described above, and their geometry is recorded. An example of flow cytometry sort analysis is described below.

EXAMPLE 4

Flow Cytomery Sort Analysis

A flow cytometer was used to extract reticulocytes and PS-exposing RBCs from whole blood. The reticulocytes were stained with a retic stain kit. Briefly, 5 µL of whole blood was dark incubated 30 min. with 1 mL of retic reagent. For PS labeling, 1 µL of blood was incubated in 400 µL binding buffer and 40 µL FITC-labeled Annexin V. The solution was incubated 15 min. in the dark, then diluted with an additional 2 mL of binding buffer.

The samples were sorted using a cell exclusion sort gate. The sorted cells were collected in BSA coated Eppendorf tubes, and spun at 4000 rpm for 5 min. The supernatant was removed, and the bottom 0.5 mL combined into a 1 mL Eppendorf tube. The tube was spun on a micro-centrifuge for 5 min. at 4000 rpm, and the top 0.8 mL removed and discarded. A typical sort yield is approximately 30,000 cells.

The samples are then placed on the micropipette array as above, and their geometry is recorded.

Flow cytometric separation provides unequivocal separation of cells into meaningful populations. It is possible to obtain young and old cell populations based on internal and external markers, rather than size and density separation methods used with the gradient array. The very young cells are identified by staining the residual mRNA in the cytoplasm. It was discovered that about 1.2% of the entire population of RBCs were identified as reticulocytes. PS (phosphatidyl serine) is an asymmetrical membrane lipid whose appearance on the membrane surface is associated with presenescent cells. The Annexin-V bind to this PS and allows the flow cytometer to identify and extract these PS exposing cells.

The results clearly showed that the surface area and volume of RBCs decreases with age, which verifies the results obtained using the gradient array. It is interesting to note that, although the surface area and volume decreases proportionately, the excess surface area diminishes more significantly with age.

Figure 5:
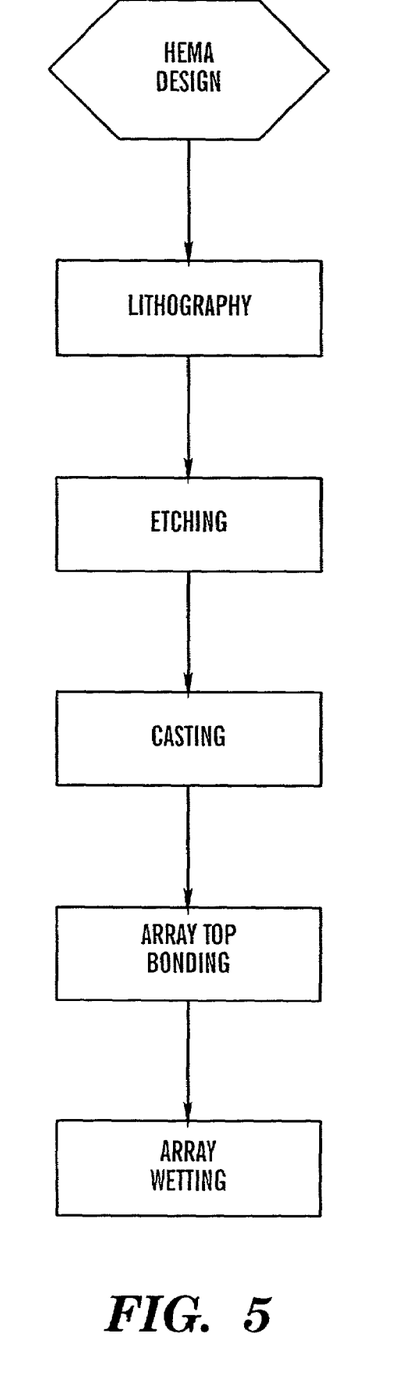
FIG. 5 is a schematic view of a preferred process for fabricating a cellular diagnostic array according to the present invention.

Referring to FIG. 5, a HEMA 20 produced according to the present invention utilizes technology developed in the semiconductor industry to create microscopic physical features, with dimensions on the same scale as human capillaries. Preferably, the design of HEMA 20 is created using a Computer Aided Design (CAD) program, which is transferred to a silicon wafer using lithography. The three-dimensional features are subsequently etched into the wafer using this pattern. The etched wafer is then used as a negative relief mold, from which multiple replicas of HEMA 20 can be cast, preferably, in silicone rubber.

In general, microfabrication of HEMA 20 can be summarized into three steps: lithography, etching, and molding.

Microfabrication of HEMA 20 begins with lithography, which is the process of transferring a pattern onto the surface of the silicon wafer substrate. The most common type of lithography is photolithography, although electron beam lithography is preferred for the present invention. Photolithography uses light to expose a pattern onto a photosensitive compound call photoresist. Electron beam lithography allows significantly smaller critical dimensions to be generated because the resolution of the beam is not limited by light wave diffraction.

The pattern can be transferred from the computer directly to the resist coated silicone wafer substrate in a process known as "direct write." No photomask is needed when using the direct write process. This has the advantage of eliminating costly mask manufacture, as well as the difficulties inherent in the scale and alignment of the mask. However, the primary limitation of direct write lithography is that each pattern must be individually scanned onto the wafer. This limits the use of direct write lithography to small production quantities and prototyping. For large scale manufacturing of silicon devices, a mask is almost always necessary.

Following lithography, etching is performed on the silicone wafer substrate. Etching is a subtractive process by which a three-dimensional structure is created within the silicone wafer substrate, often by etching around a protective masking layer, such as the photoresist. There are two basic types of etching used in micromachining: wet and dry etching. While wet etching may be employed, dry etching is preferred because it offers better control of critical dimensions, has less disposal problems, and is less corrosive to fine features on the chip.

Most kinds of dry etching use either a high-energy electric field (plasma) or a high-energy magnetic field (discharge). These dissociate trapped gasses into energetic ions, photons, electrons, and highly reactive radicals. Preferably, the etching is preformed by inductively coupled plasma, which creates high aspect ratio patterns in the silicon.

Finally, a cast then molded from the etched silicone wafer substrate. Preferably, the cast is formed using a polymeric elastomer, such as a silicone rubber polymer, which creates a disposable and substantially transparent structure. More preferably, "room temperature vulcanizing" polydimethylsiloxane is used due to its ability to flow into and adopt the shape of features with critical dimensions less than 1 µm. In addition, polydimethylsiloxane is substantially transparent, inexpensive, and biocompatible.

The following is an example of a process used to fabricate a HEMA according to the present invention.

EXAMPLE 5

Hema Fabrication

Silicon wafers with no silicone dioxide coating are cleaned on a spinner with acetone and isopropyl alcohol. The HMDS vapor prime is performed using a YES oven. The primed wafers are then spin-coated with a 1:1, UV-5: Solvent 11 positive resist mixture at 3000 rpm for 60 s, giving a thickness of 230 nm. The resist is baked on a vacuum Hotplate for 1 minute at 130° C. If the resist does not adhere to the wafer, the wafer is cleaned in a Branson Barrel Etcher for 2 min. at 1000 watts, a HDMS solution is spun on in the same manner as the resist, and the resist is spun on over this primer coating as outlined above.

A pattern is designed, preferably using a CAD program, such as the polygon editor in SYMBAD (Cadence Design Systems). The pattern design is then converted and transferred to an electron beam computer. Each prepared wafer is placed in a Leica/Cambridge EBMF 10.5. The dosage ranges from about 16 to about 28 µC/cm$^2$. The field size is set at about 3.27 mm with a pixel size of about 0.1 µm a beam current of about 50 nA, and about a 600 µm aperture. The post exposure is baked at 130° C. for 90 s. The resist is developed using CD-26 for 20 s and rinsed in deionized water. Finally, each wafer is spun-dry. Up to four arrays can be patterned into each wafer.

The developed wafers are placed in the 3 in. side of the plasmatherm SLR-ICP Bosch etcher. The standard trench etch program is used, with approximately 1 loop or cycle for each 0.5 µm of etch depth. The etch depth is tested using an alpha stepper. If the depth is insufficient, the wafer can be returned to the etcher for additional process loops.

Any remaining resist is stripped using a Branson Barrel etcher with oxygen at 1000 Watts for 4 to 7 min. The wafers are spin cleaned using ethyl alcohol on a Convac spinner. To prevent adhesion of the rubber cast, they are then spin coated with a 5% solution of Contrad 70 detergent in deionized water for 15 s at 1000 rpm increasing to 2000 rpm for 1 min.

Two-part RTV silicone rubber is mixed thoroughly in a 10:1 ratio and then placed in a vacuum desiccator at 28 Torr for 20 min. to de-gas the mixture. The TRV silicone rubber is poured over the array pattern on the leveled silicone wafer substrate. After a 5 min. settling time the elastomer is cured for 1 h at 100° C. The cooled RTV rubber array cast is then peeled from the silicon master.

A standard silica glass microscope slide is bonded to the RTV rubber array as a cover. A ⅛ inch diamond mandrill is used to drill a hole in the slide to allow suction in the array. The RTV elastomer is spread onto the slide then spun for 15 s at 1000 rpm and 1500 rpm for 60 s. The cover slide is cured like the array. The cover and the array are placed face up in a plasma cleaner/sterilizer for 1 min. at high voltage. The cover is then placed in contact with the array, forming a permanently bonded module. Immediately following bonding, a drop of HEPES buffer solution is added to the array module opening, wetting the inside of the array module.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An array comprising a plurality of individual microchannels for capturing an individual cell therein, wherein each individual microchannel includes an entry portion for receiving said cell and an exit portion that said cell may pass through, wherein the plurality of microchannels are arranged in rows and columns and wherein there are at least two rows and at least two columns, wherein the exit portion of each individual microchannel faces the entry portion of the microchannel in a successive row.

2. The array of claim 1, wherein said microchannels each have a depth of 0.8 to 6.0 microns, a length of between 10 microns to 210 microns, said length including an entry portion for receiving said individual cell and an exit portion that said individual cell may pass through, said entry portion having an entry width of between 2.5 microns to 25 microns, and said exit portion having an exit width of between 0.5 microns to 7 microns.

3. The array of claim 1, wherein said microchannels are wedge-shaped, wherein the wedge shaped microchannels have a three dimensional entry portion that is wider than a three dimensional exit portion.

4. The array of claim 2, wherein said length is about 60 microns, said entry width is about 3.7 microns, and said exit width is about 1.5 microns and depth of about 3.4 microns.

5. The array of claim 2, wherein said length is about 35 microns, said entry width is about 3.6 microns, and said exit width is about 1.4 microns.

6. The array of claim 2, wherein said length is about 100 microns, said entry width is about 4.5 microns, and said exit width is about 1.5 microns.

7. The array of claim 2, wherein said length is about 16 microns, said entry width is about 3.6 microns, and said exit width is about 1.4 microns.

8. The array of claim 1, further comprising shunt channels, wherein said shunt channels comprise individual microchannels arranged in at least one row and at least two columns, wherein said microchannels are adapted to allow said cell to enter the entry portion and exit the exit portion in order to bypass an individual microchannel occupied with a cell.

9. The array of claim 8, wherein said shunt channels have a length of between 10 microns and 100 microns.

10. The array of claim 1, wherein said microchannels have cross-sectional dimensions adapted to temporarily deform a cell passing therethrough.

11. The array of claim 1, further comprising a means for moving said cells through said microchannels.

12. The array of claim 11, wherein said means for moving said cells through said microchannels comprises a vacuum pump for pulling said cell through said microchannels, negative pressure generated by connected water columns, or a peristaltic pump for driving said cell through the channels.

13. A gradient army for analyzing a plurality of cells comprising at least three rows of microchannels and at least two columns of microchannels, wherein the microchannels have an entry portion for receiving cells and an exit portion whereby cells may pass through, wherein the exit portion of the microchannels in the first row face the entry portion of the microchannels in a second row and the exit portion of the microchannels in the second row face the entry portion of the microchannel in a third row, and wherein the width of the microchannels in the first row is wider than the cells to be analyzed such that cells enter the entry portion and exit the exit portion of the microchannels in the first row and enter the entry portion of the microchannels in the second row, and wherein the microchannels in the first row have a first width which is larger compared to the width of the microchannels in the second row, wherein cells are either trapped within a microchannel in the second row or pass through the exit portion of the microchannel in the second row and enter the entry portion of them microchannel in the third row, wherein cells that pass through the exit portion of the second row enter the entry portion of the microchannels in the third row.

14. The array of claim 3, wherein the dimensions of the wedge-shaped microchannel are defined by area and volume, wherein the area and volume of a cell are known and the length, width and height of the microchannel is varied so that a target blood cell may enter, but not exit.

15. An array comprising a plurality of individual microchannels for capturing an individual cell therein, wherein each individual microchannel includes an entry portion for receiving said cell and an exit portion that said cell may pass through, wherein the plurality of microchannels are arranged in rows and columns and wherein there are at least two rows and at least two columns, wherein the exit portion of each individual microchannel faces the entry portion of the microchannel in a successive row, wherein each individual microchannel is a wedge shape, wherein the wedge shaped microchannels have a three dimensional entry portion that is wider than a three dimensional exit portion.

* * * * *